United States Patent [19]

Coll et al.

[11] 4,336,376

[45] Jun. 22, 1982

[54] PROCESS FOR THE PREPARATION OF 7-(D(−)-ALPHA-AMINO-P-HYDROXY-PHENYLACETAMIDO)DESACETOXYCEPH-ALOSPORANIC ACID

[75] Inventors: Antonio L. P. Coll, Barcelona; José D. Meseguer, Granollers; Asunción E. Bianchini; Esteve S. Pitarch, both of Barcelona, all of Spain

[73] Assignee: Gema, S.A., Barcelona, Spain

[21] Appl. No.: 234,896

[22] Filed: Feb. 17, 1981

[30] Foreign Application Priority Data

Feb. 20, 1980 [ES] Spain ................................. 488.783

[51] Int. Cl.³ ........................................... C07D 501/04
[52] U.S. Cl. .................................... 544/030; 424/246; 544/28
[58] Field of Search .................. 544/21, 30, 28, 26, 544/27; 424/246

[56] References Cited

U.S. PATENT DOCUMENTS 4,148,817  4/1979  Wright ................................. 544/30

*Primary Examiner*—Nicholas S. Rizzo
*Attorney, Agent, or Firm*—Scully, Scott, Murphy & Presser

[57] ABSTRACT

There is described a process for the preparation of 7-(D(−)-alpha-amino-p-hydroxyphenylacetamido)-desacetoxycephalosporanic acid in which a D(−)-p-hydroxy-N-(1-alcoxycarbonyl-2-propenyl)-alpha-aminophenylacetic acid salt is reacted with trimethylsilyl-2-oxazolidinone. The resulting reaction product is reacted in turn with an acyl chloride or an alkyl chloroformate to give a mixed anhydride which is reacted with a solution of 7-aminodesacetoxycephalosporanic acid prepared by silylation, in an anhydrous organic solvent, with trimethylsilyl-2-oxazolidinone.

5 Claims, No Drawings

PROCESS FOR THE PREPARATION OF 7-(D(−)-ALPHA-AMINO-P-HYDROXY-PHENYLACETAMIDO)DESACETOXYCEPH-ALOSPORANIC ACID

FIELD OF THE INVENTION

The present invention relates to a process for the preparation of 7-(D(−)-alpha-amino-p-hydroxy-phenylacetamido)desacetoxycephalosporanic acid having the structural formula:

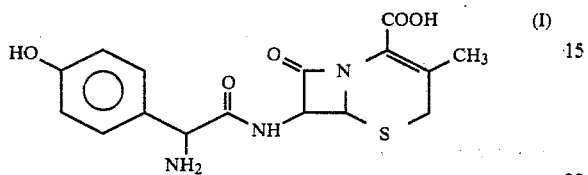

a product known as p-hydroxycephalexin or cephadroxyl and is of interest in human and veterinary medicine.

DESCRIPTION OF THE PRIOR ART

The methods for the preparation of p-hydroxycephalexin may be divided into the following classes as far as the acylation is concerned:

(a) the use of a mixed anhydride prepared by reaction of a D(−)-2p-hydroxyphenylglycine salt, having the amino group blocked preferably as enamine, with an acyl chloride or with an alkylchloroformate (U.S. Pat. No. 3,985,741).

(b) the use of D(−)-2-p-hydroxyphenylglycine chloride-hydrochloride. In this case, the difficulty lies in the isolation of this activated form of the acid, which is not attainable by conventional methods (U.S. Pat. Nos. 3,925,418 and 3,980,637).

Generally speaking, the dissolution of 7-aminodesacetoxycephalosporanic acid (7-ADCA) is attained by formation of basic salts in aqueous media. A further technique used is silylation, which may be carried out with different silylating agents and which leads to binary systems of monosilylated and disilylated 7-ADCA.

SUMMARY OF THE INVENTION

A new process has now been discovered for the manufacture of p-hydroxycephalexin (I), the most important features of which may be summed up hereinafter:

(1) Selective silylation of the D(−)-2-hydroxyphenylglycine phenol group with the amino group blocked as enamine, as disclosed in Spanish Pat. No. 459,494. For this purpose, trimethylsilyl-2-oxazolidinone (TMSO) having the formula:

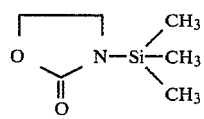

a reactant disclosed in Spanish Pat. No. 411,867, has been considered to be most appropriate.

The blocking of the phenol group inhibits competition reactions in which the —OH group is inevitably involved, both in the mixed anhydride formation step and in the later acylation step. With silylation, not only the yield but also the quality of the finished product is increased.

(2) Reaction of a D(−)-p-trimethylsiloxyphenylglycine salt, having the amino group blocked as enamine, with an acyl chloride or alkyl chloroformate to give the following mixed anhydride:

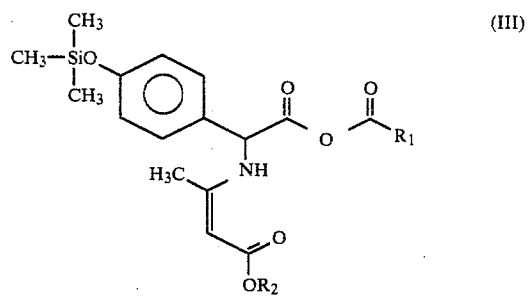

in which $R_1$ may be: —OCH$_2$CH$_3$, —OCH$_3$, phenyl or $C_4$–$C_9$ alkyl groups and $R_2$ is ethyl or methyl.

(3) Silylation of 7-aminodesacetoxycephalosporanic acid (7-ADCA) of formula IV with TMSO of formula II, in an anhydrous organic solvent.

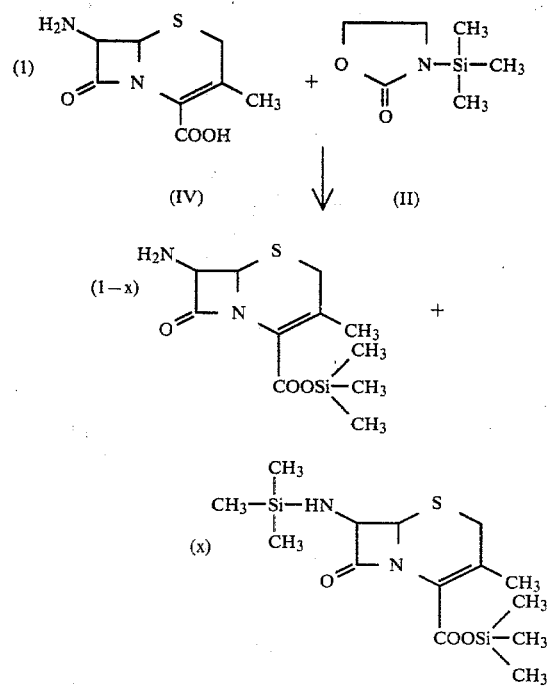

(4) Reaction of the mixed anhydride of formula III with a solution of silylated 7-ADCA in an anhydrous medium which, after the unblocking and precipitation step, leads to the preparation of p-hydrocephalexin or cephadroxyl.

The importance of carrying out all the reactions in anhydrous organic solvent lies in the inhibition of the beta-lactam ring degradation processes, particularly promoted in aqueous media and above all under basic conditions ("Cephalosporins and Penicillins" E. H. Flynn, Academic Press Inc., New York, 1972, page 105 et seq.).

Thus the object of the invention is a process for the preparation of p-hydroxycephalexin (cephadroxyl), characterised essentially by reacting one equivalent of a D(—)-p-hydroxy-N-(1-alcoxycarbonyl-2-propenyl)-alpha-aminophenylacetic acid salt with one equivalent of trimethylsilyl-2-oxazolidinone (TMSO) to give a compound having the following general formula:

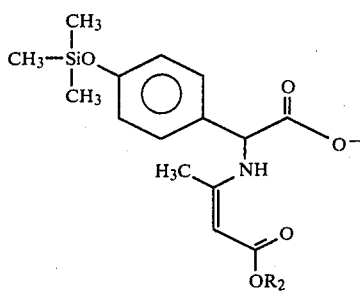  (V)

which is reacted with a compound of the general formula:

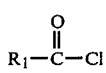  (VI)

such as an acyl chloride or an alkyl chloroformate, to give a mixed anhydride having the following general formula:

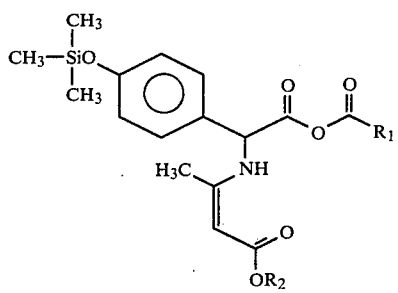  (III)

in which $R_1$ and $R_2$ are as hereinbefore defined. The said mixed anhydride of formula III is reacted with a solution of silylated 7-ADCA to give p-hydroxycephalexin (cephadroxyl) after the unblocking and precipitation step

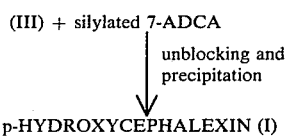

p-HYDROXYCEPHALEXIN (I)

Particularly outstanding features of this invention are:

(a) the use of the mixed anhydride of formula III with the phenyl group selectively protected with the trimethylsilyl group, thereby preventing competition reactions and promoting the formation of the mixed anhydride by considerations of solubility.

(b) the use of strictly anhydrious media which inhibit beta-lactam ring degradation processes and competition reactions.

All of the foregoing leads to the preparation of p-hydroxycephalexin, with excellent yield and quality.

Graphically illustrated, the new process for the preparation of p-hydroxycephalexin is developed according to the following scheme:

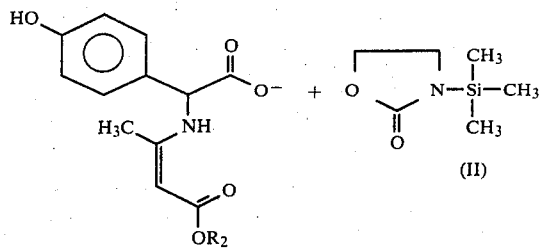  (II)

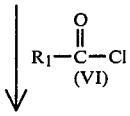  (VI)

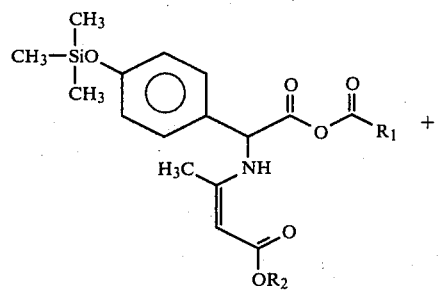  (III)

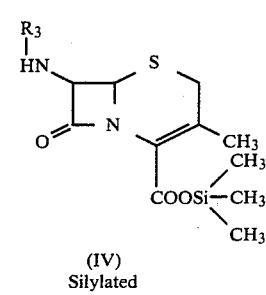

(IV) Silylated

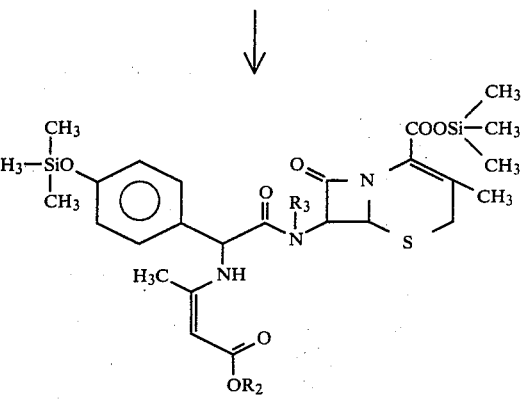

(I)

in which $R_1$ and $R_2$ are as hereinbefore defined and $R_3$ is hydrogen or a trimethylsilyl group.

EXAMPLE 1

7(D(−)-alpha-amino-p-hydroxyphenylacetamido)-desacetoxycephalosporanic acid

Trimethylsilyl-2-oxazolidinone (3.2 ml, 2.082 cmoles) was added to a suspension of D(−)-p-hydroxy-N-(1-methoxycarbonyl-2-propenyl)-alpha-aminophenylacetic acid potassium salt (6.31 g, 2.082 cmoles) in acetonitrile (50 ml). There was obtained a fluid suspension which was stirred for 40 minutes. It was chilled to −20° C. and pivaloyl chloride (2.64 ml, 2.134 cmoles) was added. An immediate fluidification was observed, giving a cream coloured fluid suspension which was stirred for 30 minutes at −10° C.

A solution of 7-aminodesacetoxycephalosporanic acid (3.6 g, 1.69 cmoles), acetonitrile (50 ml) and trimethylsilyl-2-oxazolidinone (11.3 ml, 7.38 cmoles) was prepared with refluxing for 10 minutes. The resultant ochre coloured solution was cooled to room temperature and added over the above suspension chilled to −15° C. over a period of 30 minutes. A cream coloured suspension, which was stirred for 2 hours at −10° C., was obtained.

Thereafter methanol (25 ml) was added and the mixture was stirred for 10 minutes at 0°/−5° C. It was filtered through a filter aid to remove the unreacted KCl and 7-ADCA. The filter was washed with acetonitrile and the filtrates were chilled to 0° C., and water was added (25 ml). The ochre coloured solution was adjusted to pH 2 with hydrochloric acid and was stirred for 20 minutes at 0°-5° C., pH 2. The pH was raised to 5.5 with the addition of triethylamine (TEA) at room temperature. There was obtained a suspension which was stirred for 90 minutes at room temperature. It was filtered, washed with acetonitrile (40 ml) and dried, to give the compound of the title (p-hydroxycephalexin).

EXAMPLE 2

Following Example 1, but replacing the pivaloyl chloride with benzoyl chloride (2.48 ml, 2.134 cmoles), p-hydroxycephalexin was prepared.

EXAMPLE 3

Following Example 1, but replacing the D(−)-p-hydroxy-N-(1-methoxycarbonyl-2-propenyl)-alpha-aminophenylacetic acid potassium salt with D(−)-p-hydroxy-N-(1-ethoxycarbonyl-2-propenyl)-alpha-aminophenylacetic acid potassium salt (6.602 g, 2.082 cmoles), p-hydroxycephalexin was obtained.

EXAMPLE 4

Following Example 1, but replacing the pivaloyl cloride with ethyl chloroformate (2.03 ml, 2.134 cmoles), p-hydroxycephalexin was prepared.

EXAMPLE 5

Example 1, was followed but the 7-aminodesacetoxycephalosporanic acid was dissolved as explained below. Trimethylsilyl-2-oxazolidinone (6.46 ml, 4.225 cmoles) was added to a suspension of 7-aminodesacetoxycephalosporanic acid (3.6 g, 1.69 cmoles) in acetonitrile (50 ml) and was refluxed for 45 minutes. p-hydroxycephalexin was obtained.

EXAMPLE 6

Following Example 1, but replacing the pivaloyl chloride with methyl chloroformate (1.65 ml, 2.134 cmoles), p-hydroxycephalexin was obtained.

What we claim is:

1. A process for the preparation of 7-(D(−)-alpha-amino-p-hydroxyphenylacetamido)desacetoxycephalosporanic acid, which comprises:

(a) reacting one equivalent of a sodium or potassium salt of D(−)-p-hydroxy-N-(1-alkoxycarbonyl-2-propenyl)-alpha-aminophenylacetic acid with one equivalent of trimethylsilyl-2-oxazolidinone at a temperature of from 20° to 25° C., to provide a compound V of the general formula:

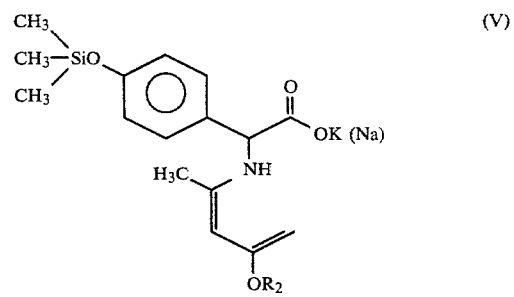

in which $R_2$ may be ethyl or methyl;

(b) reacting in situ the compound of general formula V with a compound VI of the general formula:

to provide a solution containing a mixed anhydride III of the general formula:

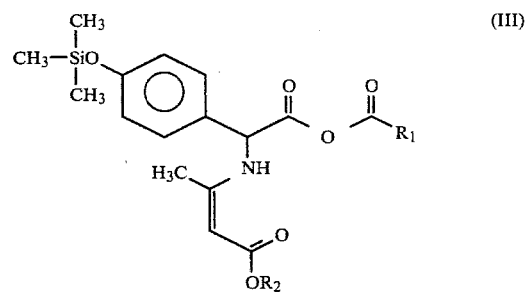

in which $R_1$ may be methoxy, ethoxy, phenyl or a $C_4$-$C_9$ aliphatic chain;

(c) reacting in situ said mixed anhydride of general formula III with silylated 7-aminodesacetoxycephalosporanic acid, obtained by silylation in acetonitrile with trimethylsilyl-2-oxazolidinone, to provide a solution containing a compound of the general formula:

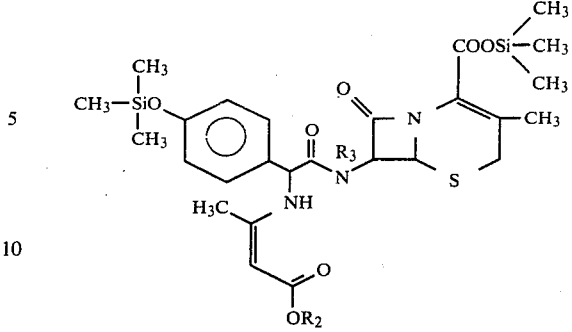

in which $R_3$ is a hydrogen atom or a trimethylsilyl group, followed by unblocking in situ and precipitation to provide 7-(D(−)-alpha-amino-p-hydroxyphenylacetamido)desacetoxycephalosporanic acid.

2. The process of claim 1, wherein the compound of the general formula IV is an acyl chloride.

3. The process of claim 2, wherein the acyl chloride is chosen from among the group formed by pivaloyl chloride and benzoyl chloride.

4. The process of claim 1, wherein the compound of the general formula IV is an alkyl chloroformate.

5. The process of claim 1, wherein the alkyl chloroformate is chosen from among the group formed by ethyl chloroformate and methyl chloroformate.

* * * * *